(12) United States Patent
Liu et al.

(10) Patent No.: US 10,732,154 B2
(45) Date of Patent: Aug. 4, 2020

(54) TWO-DIMENSIONAL LIQUID CHROMATOGRAPHY

(71) Applicant: The Board of Regents of the University of Oklahoma, Norman, OK (US)

(72) Inventors: Shaorong Liu, Norman, OK (US); Zaifang Zhu, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 201 days.

(21) Appl. No.: 15/913,043

(22) Filed: Mar. 6, 2018

(65) Prior Publication Data
US 2018/0259495 A1  Sep. 13, 2018

Related U.S. Application Data

(60) Provisional application No. 62/467,936, filed on Mar. 7, 2017.

(51) Int. Cl.
| | |
|---|---|
| *G01N 30/16* | (2006.01) |
| *C07K 1/16* | (2006.01) |
| *G01N 30/60* | (2006.01) |
| *G01N 1/40* | (2006.01) |
| *G01N 33/68* | (2006.01) |
| *G01N 30/46* | (2006.01) |
| *G01N 35/10* | (2006.01) |
| *G01N 30/02* | (2006.01) |

(52) U.S. Cl.
CPC .......... *G01N 30/6034* (2013.01); *C07K 1/16* (2013.01); *C07K 1/165* (2013.01); *G01N 1/4077* (2013.01); *G01N 30/16* (2013.01); *G01N 30/463* (2013.01); *G01N 33/6842* (2013.01); *G01N 35/1097* (2013.01); *G01N 30/466* (2013.01); *G01N 2030/027* (2013.01)

(58) Field of Classification Search
CPC .... G01N 30/96; G01N 30/6034; G01N 30/16; G01N 30/463; G01N 35/1097; G01N 1/4077; G01N 33/6842; G01N 30/466; G01N 2030/027; B01D 15/186; C07K 1/16; C07K 1/165
USPC ......................................... 436/79; 210/198.2
See application file for complete search history.

(56) References Cited

U.S. PATENT DOCUMENTS 6,358,692 B1 * 3/2002 Jindal .................. G01N 30/461
435/7.1

* cited by examiner

*Primary Examiner* — Jennifer Wecker
*Assistant Examiner* — Michael Paul Shimek
(74) *Attorney, Agent, or Firm* — Dunlap Codding, P.C.

(57) ABSTRACT

A two-dimensional liquid chromatography (2D-LC) apparatus and method of its use, the apparatus constructed with (1) a first dimension (first-D) having at least one first chromatography column, (2) at least one multi-port stream selector in fluid communication with the at least one first chromatography column for receiving an effluent therefrom, and (3) a second dimension (second-D) having a plurality of second chromatography columns, each second chromatography column in fluid communication with a corresponding port of the at least one multi-port stream selector for receiving an effluent fraction of the effluent from the at least one first chromatography column, thereby enabling simultaneous chromatographic separation by the plurality of second chromatography columns of a set of multiple effluent fractions outputted from the at least one first chromatography column.

6 Claims, 17 Drawing Sheets
(2 of 17 Drawing Sheet(s) Filed in Color)

TWO-DIMENSIONAL LIQUID CHROMATOGRAPHY

CROSS-REFERENCE TO RELATED APPLICATIONS

This application claims priority to U.S. Provisional Application No. 62/467,936, filed on Mar. 7, 2017, which is expressly incorporated herein by reference in its entirety.

BACKGROUND

In proteomic research, two complementary approaches (bottom-up and top-down) are commonly used for protein analysis. The bottom-up approach has progressed rapidly due to the advancement of modern mass spectrometry (MS), enabling identification and quantitation of hundreds or even thousands of proteins in single analysis. However, this approach can miss the information of post-transitional modification, mutations and proteolytic cleavage, and therefore other approaches are constantly sought. The top-down approach is a great alternative, in which intact proteins are individually analyzed. One of the most challenging tasks in the latter approach is to isolate proteins from a background of many other proteins and complex matrices. Often, this is beyond the resolving power of a one-dimensional separation technique. Vast effort has been invested on exploiting multi-dimensional separation strategies and progress has been made recently.

Two-dimensional electrophoresis (2DE) is a powerful method for separating intact proteins. It quickly became routine after its introduction in 1975. However, extracting individual proteins after 2DE separation is tedious and time-consuming. In the last decade or so, two-dimensional liquid chromatography (2D-LC), also referred to herein as two-dimensional high performance liquid chromatography (2D-HPLC), has received considerable attention due to its attractive features such as great number of chromatography mode choices, high resolving power, convenience for collecting resolved-proteins, and straightforwardness for automating 2D HPLC.

While some 2D HPLC techniques analyze only portions of the first dimension (first-D) effluents, a comprehensive 2D HPLC analyzes all of them, preventing losses of any proteins. One of the early comprehensive 2D HPLC systems was constructed by Bushey and Jorgenson (Bushey, M. M. & Jorgenson, J. W. Automated instrumentation for comprehensive two-dimensional high-performance liquid chromatography of proteins. *Anal. Chem.* 62, 161-167 (1990)). Through an eight-port valve, these authors coupled cation exchange and size exclusion chromatography for intact protein separations.

A major challenge in current 2D HPLC is the limited separation speed in the second dimension (second-D). Because current 2D HPLC systems employ one first-D column and one second-D column, the first-D effluent is fractionated and sequentially analyzed by the second-D. In order to retain the first-D resolution, one has to fractionate its effluent frequently (or in small segments) to minimize the re-mixing of the resolved analytes. Often, the effluent fractions must be parked somewhere for later or off-line analyses, resulting in a slow and tedious analysis of the sample. An improved 2D HPLC process which results in faster separation would be desirable. It is to this goal that the novel technology of the present disclosure is directed.

BRIEF DESCRIPTION OF THE DRAWINGS

Several embodiments of the present disclosure are hereby illustrated in the appended drawings. It is to be noted however, that the appended drawings only illustrate several embodiments and are therefore not intended to be considered limiting of the scope of the present disclosure.

The patent or application file contains at least one drawing executed in color. Copies of this patent or patent application publication with color drawing(s) will be provided by the Office upon request and payment of the necessary fee.

DETAILED DESCRIPTION

Figure 1A:
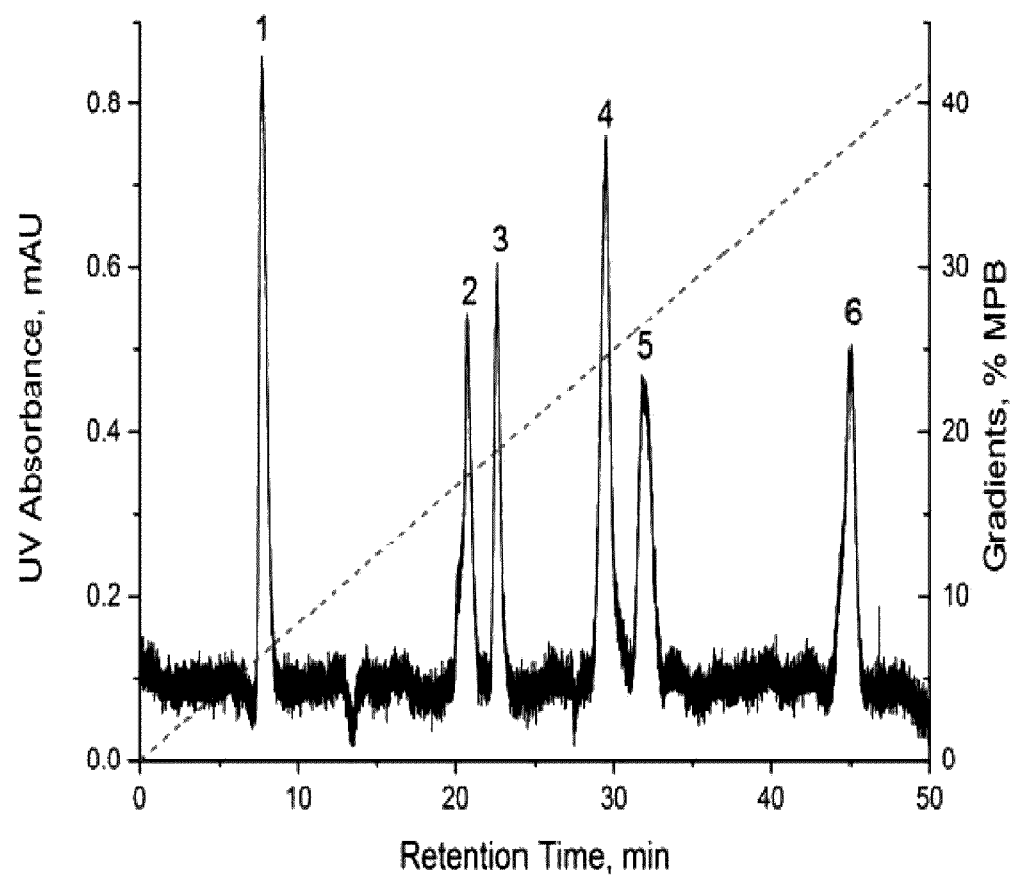
FIG. 1A. Performance of IEX chromatography: Separation of protein standards. The column was a monolithic one made in laboratory. It was of 20-cm length, 360-μm o.d. and 250-μm i.d. Mobile phase A, 10 mM Tris/HCl at pH ~7.6 in DDI water; mobile phase B, 1 M NaCl dissolved in mobile phase A. Gradient, as indicated with the dashed line in the figure; detection, UV at 280 nm; injection volume, 20 μL; sample, a mixture of a-lactalbumin (1), trypsin inhibitor (2), phosphorylase b (3), carbonic anhydrase (4), ovalbumin (5), and transferrin (6); each at 0.3 μg/mL; pressure on column, ~1200 psi.

A new two-dimensional (2D) high performance liquid chromatography (HPLC) approach for intact protein analysis has been developed. As noted above, because current 2D HPLC systems employ one first-D column and one second-D column, the first-D effluent is fractionated and sequentially analyzed by the second-D. In order to retain the first-D resolution, one has to fractionate its effluent frequently (or in small segments) to minimize the re-mixing of the resolved analytes. Often, the effluent fractions must be parked somewhere for later or off-line analyses, resulting in a slow and tedious analysis of the sample. The novel apparatus and methods of the present disclosure overcome this problem by incorporating multiple ("n") columns at least in the second-D stage. While the effluent of the first-D is loaded into one of the "n" second-D columns, separations in other second-D columns proceed simultaneously, speeding up the analysis process and resulting in a reduction of the time requirement of the second-D separation by a factor of n. The apparatus and process is described in further exemplary detail below.

Before further describing various embodiments of the present disclosure in more detail by way of exemplary description, examples, and results, it is to be understood that the embodiments of the present disclosure are not limited in application to the details as set forth in the following description. The embodiments of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. The embodiments of and application and use thereof can be made and executed without undue experimentation in light of the present disclosure. While the present disclosure has been described in terms of particular embodiments, it will be apparent to those of skill in the art that variations may be applied to the apparatus and/or methods and in the steps or in the sequence of steps of the methods described herein without departing from the concept, spirit, and scope of the inventive concepts as described herein. All such similar substitutes and modifications apparent to those having ordinary skill in the art are deemed to be within the spirit and scope of the inventive concepts as disclosed herein.

All patents, published patent applications, and non-patent publications referenced or mentioned in any portion of the present specification are indicative of the level of skill of those skilled in the art to which the present disclosure pertains, and are hereby expressly incorporated by reference in their entirety to the same extent as if the contents of each individual patent or publication was specifically and individually incorporated herein.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the apparatus, methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the terms "at least one" or "plurality" will be understood to include one as well as any quantity more than one, including but not limited to, 2, 3, 4, 5, 6, 7, 8, 9, 10, 15, 20, 30, 40, 50, 100, or any integer inclusive therein, and/or any range described herein. The terms "at least one" or "plurality" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the objects, or study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-30 therefore includes 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, as well as sub-ranges within the greater range, e.g., for 1-30, sub-ranges include but are not limited to 1-10, 2-15, 2-25, 3-30, 10-20, and 20-30. Reference to a range of 1-50 therefore includes 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, etc., up to and including 50. Reference to a series of ranges includes ranges which combine the values of the boundaries of different ranges within the series. Thus, to illustrate reference to a series of ranges, for example, a range of 1-1,000 includes, but is not limited to, 1-10, 2-15, 2-25, 3-30, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. The range 3 mm to 25 cm therefore refers to and includes all values or ranges of values, and fractions of the values and integers within said range, including for example, but not limited to, 4 mm to 22.5 cm, 4 mm to 20 cm, 6 mm to 22 cm, 6 mm to 20 cm, 10 mm to 17 cm, 7.5 nm to 20 cm, 7.5 nm to 10 cm, 5 mm to 16 mm, 4 mm to 20 mm, and 8 mm to 12 cm. Any two values within the range of 3 mm to 25 cm therefore can be used to set the lower and upper boundaries of a range in accordance with the embodiments of the present disclosure.

By "biologically active" is meant the ability to modify the physiological system of an organism without reference to how the active agent has its physiological effects.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

Turning to the apparatus, systems, and methods presently disclosed, the disclosure is directed to, in certain embodiments, two-dimensional liquid chromatography (2D-LC), e.g., 2D-HPLC, systems comprising a first dimension (first-D) which comprises at least one first column (e.g., 1-10), and a second dimension (second-D) comprising a plurality of columns (such as, but not limited to, 2-50) in fluid communication with the first-D column(s) via at least one stream selector for simultaneously separating effluent fractions outputted from the first-D.

To demonstrate the feasibility of the approach of the present disclosure, an exemplary, non-limiting, 2D HPLC apparatus with three second-D columns was constructed and implemented with samples of both proteins standards, and $E.$ $coli$ lysates (Example 1). As noted above, the bottleneck for current 2D HPLC is the limited speed of the second-D separation step. This problem is solved herein by incorporating multiple second-D columns to allow a plurality of second-D separations to be conducted in parallel. In at least one non-limiting embodiment, ion-exchange chromatography (IEX) is used as the first-dimension (first-D) and reversed-phase (RP) chromatography is used as the second-D, and three second-D columns are incorporated so that three RP separations can be performed simultaneously. This system was used to separate both standard proteins and real-world samples ($E.$ $coli$ lysates), and baseline resolutions for standard proteins were achieved. For example, more than 500 protein peaks for $E.$ $coli$ lysates were obtained, even using just three second-D columns. Effluents of the second-D were collected for an $E.$ $coli$ lysate separation and the number of proteins in the collected solutions was determined by sodium dodecylsulfonate-polyacrylamide gel electrophoresis. No more than a few proteins were found in each of these samples, enabled a facile analysis by mass spectrometry. This approach can be used as a technique in proteomic research. In an alternate embodiment, a 2D-LC apparatus was constructed with 12 columns in the second-D, supplied by two multi-port stream selectors, each of which was in fluid communication with the first-D and six of the second-D columns.

Thus, in at least certain embodiments, the present disclosure is directed to a two-dimensional liquid chromatography (2D-LC) apparatus, comprising (1) a first dimension (first-D) comprising at least one first chromatography column, (2) at least one multi-port stream selector in fluid communication with the at least one first chromatography column for receiving an effluent therefrom, and (3) a second dimension (second-D) comprising a plurality of second chromatography columns, each second chromatography column in fluid communication with a corresponding port of the at least one multi-port stream selector for receiving an effluent fraction of the effluent from the at least one first chromatography column, thereby enabling simultaneous chromatographic separation by the plurality of second chromatography columns of a set of multiple effluent fractions outputted from the at least one first chromatography column.

In certain embodiments, the mode of chromatography of the first dimension of the 2D-LC apparatus of the present disclosure can be selected from size exclusion chromatography, ion exchange chromatography, normal phase chromatography, reversed phase chromatography, hydrophilic interaction chromatography, hydrophobic interaction chromatography, affinity chromatography, argentation chromatography, and critical condition chromatography. In certain embodiments, the mode of chromatography of the second dimension of the 2D-LC apparatus of the present disclosure can be selected from size exclusion chromatography, ion exchange chromatography, normal phase chromatography, reversed phase chromatography, hydrophilic interaction chromatography, hydrophobic interaction chromatography, affinity chromatography, argentation chromatography, and critical condition chromatography, wherein when the two dimensions have the same mode of chromatography (e.g., reversed phase), the two dimensions have different separation selectivities.

The inventive concepts of the present disclosure will be more readily understood by reference to the following examples and embodiments, which are included merely for purposes of illustration of certain aspects and embodiments thereof, and are not intended to be limitations of the disclosure in any way whatsoever. Those skilled in the art will promptly recognize appropriate variations of the apparatus, compositions, components, procedures and method shown below.

Example 1

Methods
Reagents
Fused-silica capillaries were products of Polymicro Technologies Inc. (Phoenix, Ariz.). Tetrahydrofuran, 1-propanol, 1,4-butanediol, 1-decanol, 2,2'-azobisisobutyronitrile (AIBN, 98%), and protein standards were obtained from Sigma (St. Louis, Mo.). Hydrochloric acid, sodium chloride, sodium hydroxide, tris(hydroxyl-methyl)aminomethane (Tris), and ethylenediamine-tetraacetic acid (EDTA) were obtained from Fisher Scientific (Fisher, Pa.). Ethylene glycol dimethacrylate (EDMA, 98%), glycidyl methacrylate (GMA, 97%), styrene (99%), divinylbenzene (80%), and diethylamine were purchased from Alfa Aesar (Ward Hill, Mass.). Methanol, acetonitrile, and tetrafluoric acid were products of EMD Chemicals, Inc. (Gibbstown, N.J.). Methacryloyloxypropyltrimethoxysilane (γ-MAPS, 98%) was purchased from Acros (Fairlawn, N.J.). All solutions were prepared with ultrapure water purified by a NANO pure infinity ultrapure water system (Barnstead, Newton, Wash.).

Preparation of Reverse-Phase (RP)-HPLC Monolith
The inner wall of a capillary (120 cm length×250 μm i.d.×360 μm o.d.) was vinylized. A 30-cm-long vinylized capillary section was filled with a mixture composed of 48 μL styrene, 48 μL divinylbenzene, 130 μL decanol, 20 μL tetrahydrofuran, and 10 μg/L AIBN. The mixture was polymerized in a water bath at 60° C. for 20 h. After polymerization, ~2 cm of the capillary at both ends was cut off and discarded. The monolith was then rinsed with acetonitrile at ~800 psi for 4 h and deionized water at ~1500 psi for 1 h.

Preparation of Ion Exchange (IEX) Monolith
A 30-cm-long piece of vinylized capillary (250 μm i.d.× 360 μm o.d.) was filled with a mixture comprising 225 μL GMA, 75 μL EDMA, 250 μL 1-propanol, 400 μL 1,4-butadiol, 50 μL deionized water, and 10 μg/μL AIBN. The polymerization was processed in a water bath at 60° C. for 16 h. After ~2 cm of the capillary at both ends was cut off, the monolith was washed with methanol at 800 psi for 4 h. Tertiary-amine groups were then created in the monolith via a ring-opening reaction of epoxy groups. 1 M diethylamine in methanol was pressurized through the above monolith in an oven at 75° C. with a 500-psi pressure for 2 h. The modified monolith was then flushed with methanol at room temperature with methanol at 800 psi for 1 h and deionized water at 1500 psi for 30 min.

Sample Preparation 2.0 mg/mL stock solutions of protein standards were prepared by dissolving the appropriate amount of protein powder in deionized water. The stock solutions were stored at a ultra-low temperature freezer. Test solutions were produced by diluting the stock solution to the desired concentrations with the mobile phase A for IEX or RP-HPLC. The *E. coli* [a transformant of BL21(DE3) competent cell] was grown in a complete Luria-Bertani medium at 37° C. overnight. Bacteria cells were harvested by centrifugation at 13,000 rpm for 5 min. Approximately 800 mg of wet bacteria pallet was suspended in 10 mL chilled sample buffer at pH ~7.6 containing 50 mM Tris-HCl, 1 mM EDTA, and 1 mM 2-mercaptoethanol. The suspended cells were finally sonicated in an ice bath by 3 cycles of 30-s bursts with 30-s cooling intervals (amplitude 55%, cycle 0.5 in a Branson Sonifier 450 W). The soluble proteins in the supernatant were collected by centrifugation at 13000 rpm for 10 min. The obtained protein lysates were directly analyzed without further purification.

Online 2D HPLC Platform

Figure 5A:
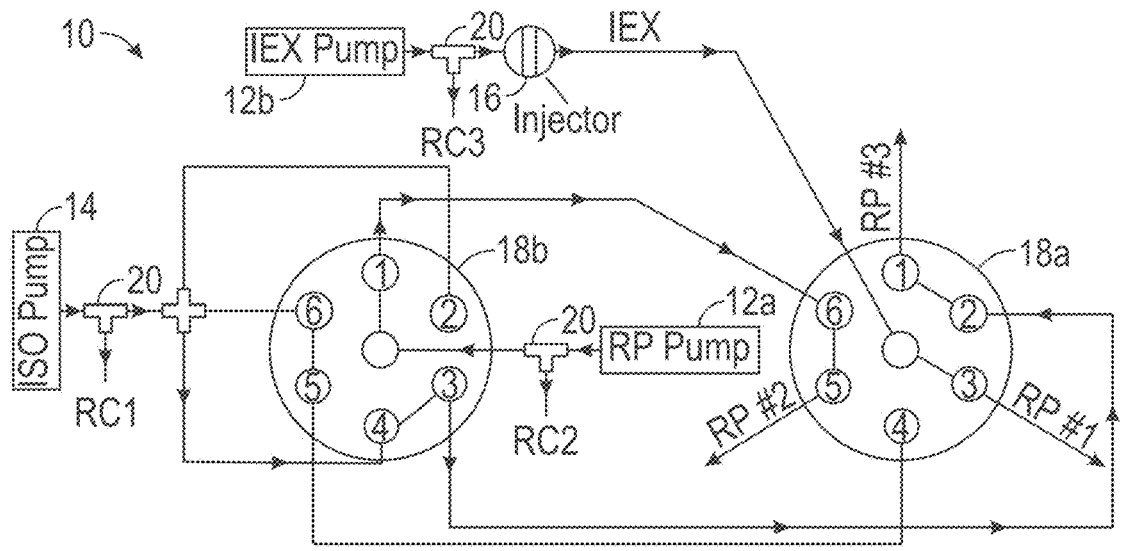
FIG. 5A is a schematic diagram of a 2D HPLC apparatus in a first mode of operation.
Figure 5B:
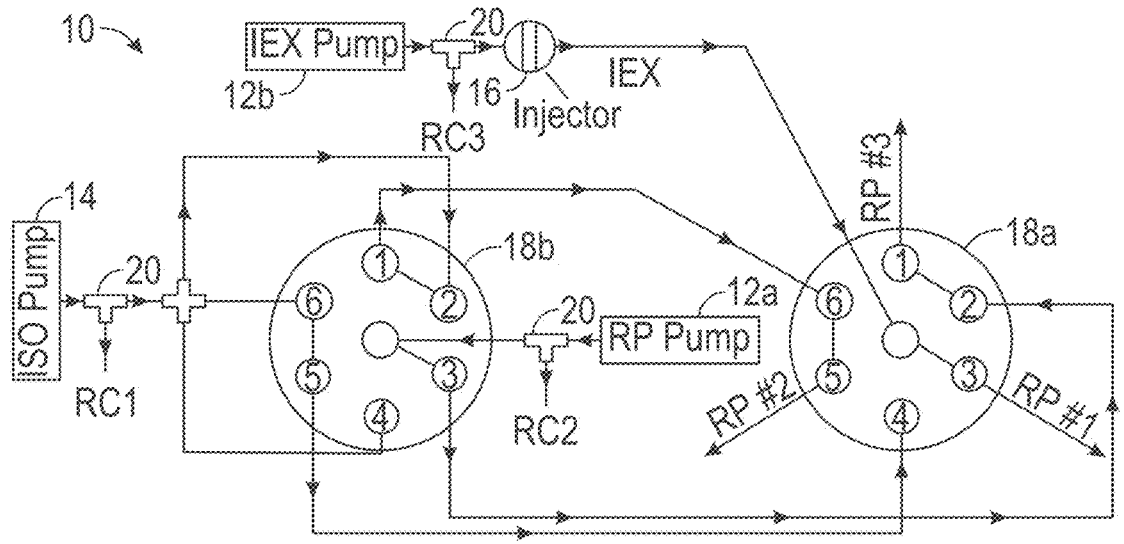
FIG. 5B is a schematic diagram of the 2D HPLC apparatus in a second mode of operation.

A schematic diagram of the 2D HPLC apparatus 10 is represented in FIGS. 5A-5B. RP #1, #2, and #3 are three parallel monolithic columns for reverse-phase high performance liquid chromatography. RC represents restriction capillaries, which are used to control the back pressure on respective columns. The apparatus 10 included two gradient pumps 12a and 12b (RP Pump—Agilent 1200 Series Binary Pump, and IEX Pump—Dionex GP50 Gradient Pump), one isocratic pump 14 (ISO pump—Jasco PU-1580 Intelligent Pump), one 20-μL injector 16, two flow-through stream selectors 18a and 18b (Valco Instruments, Houston, Tex.), and three UV/Vis detectors 20 (Linear Instruments, Reno, Nev.). The IEX Pump was used for gradient IEX and the RP Pump for RP HPLC separations. ISO Pump was used for equilibrating columns with an equilibration solution. In the first-D, intact proteins were separated using a laboratory-made IEX monolith column, and the effluent was injected directly, continuously and alternately into the three second-D RP-HPLC columns.

2D HPLC Separation

Figure 5C:
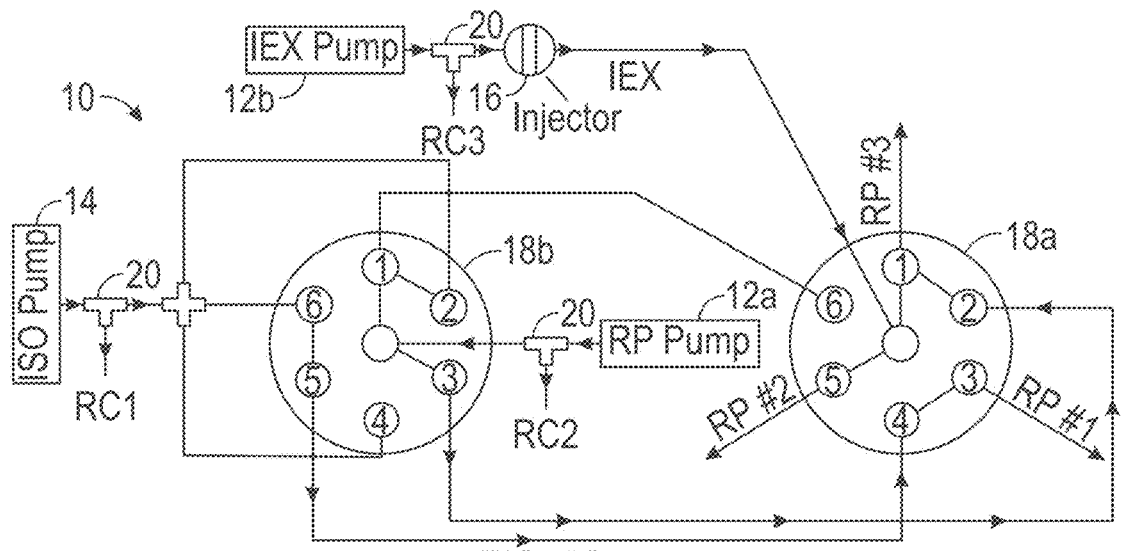
FIG. 5C is a schematic diagram of the 2D HPLC apparatus in a third mode of operation.
Figure 5D:
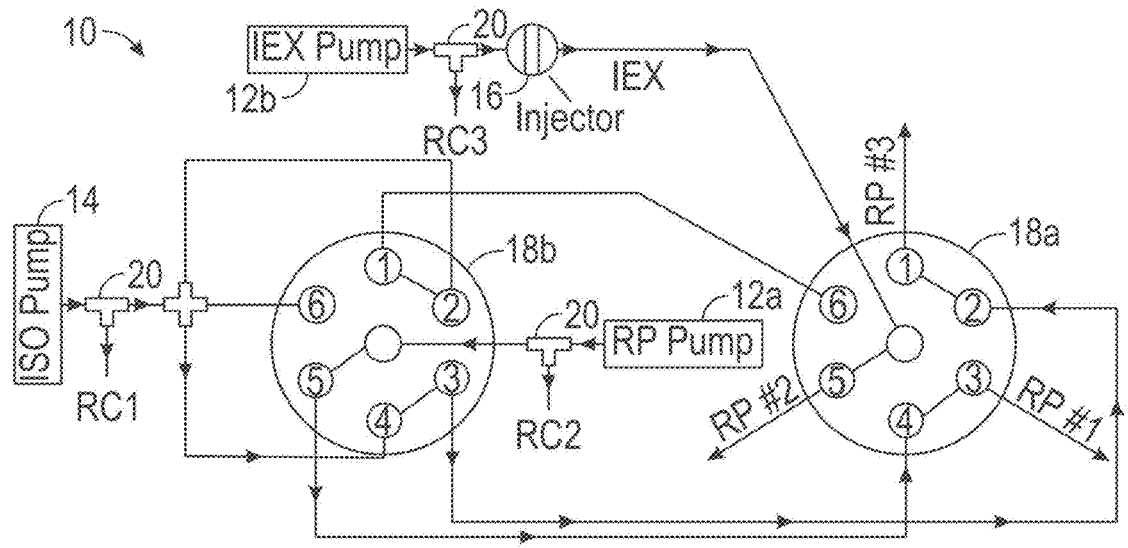
FIG. 5D is a schematic diagram of the 2D HPLC apparatus in a fourth mode of operation.
Figure 5E:
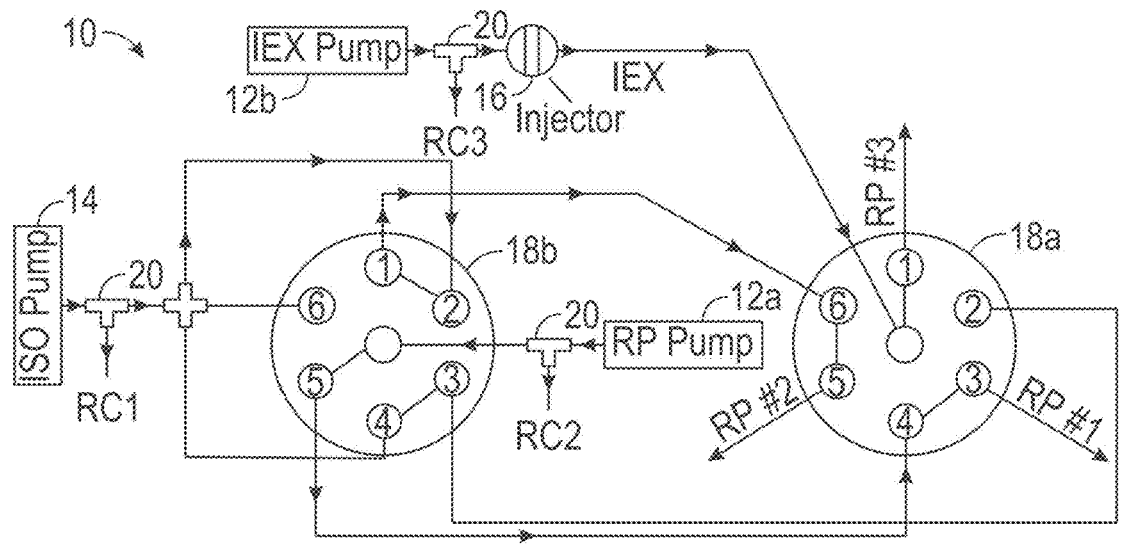
FIG. 5E is a schematic diagram of the 2D HPLC apparatus in a fifth mode of operation.
Figure 5F:
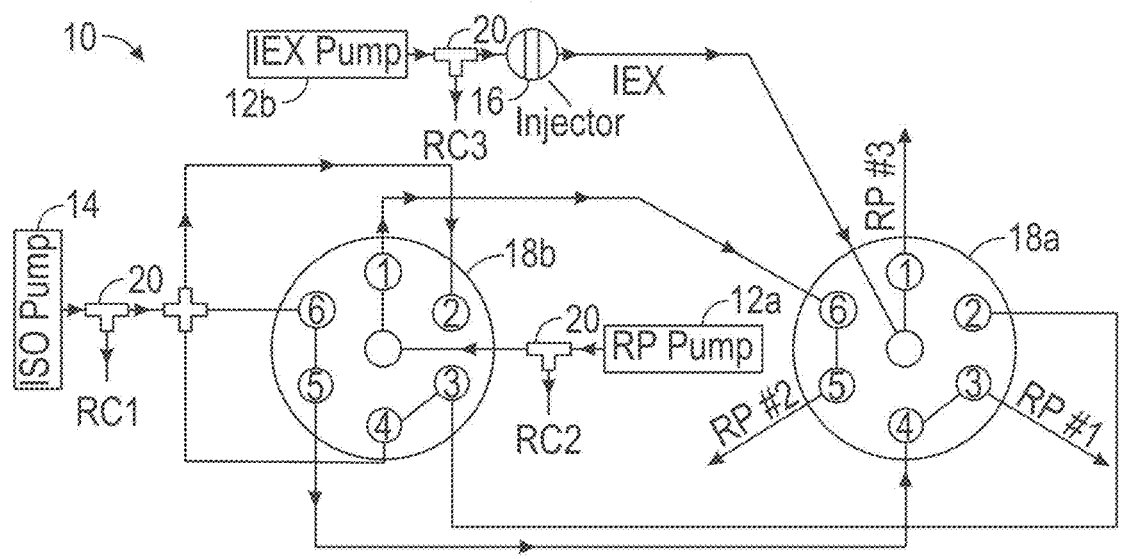
FIG. 5F is a schematic diagram of the 2D HPLC apparatus in a sixth mode of operation.

All three second-D columns were washed with an equilibration solution [5% (v/v) acetonitrile and 0.2% (v/v) tetrafluoric acid in DI water] for five minutes before a 2D HPLC separation was started. Once the gradient separation in the first-D was initiated (t=0 min), the system was set to a configuration as shown in FIG. 5A. From t=0 min to t=5 min, the first-D effluent was loaded into RP #1 column while an equilibration solution was flushing through RP #3 column and a gradient eluent was running through RP #2 column. From t=5 min to t=15 min, the left stream selector 12b was switched to Position 3 (see FIG. 5B). While the first-D effluent was still loaded into RP #1, an equilibration solution was driven through RP #2 to prepare it for sample loading. At this time, a gradient eluent was running through RP #3; if RP #3 had been loaded with a sample, a gradient elution would have started by now. From t=15 min to t=20 min, the right stream selector 12a was switched to Position 5 (see FIG. 5C). The first-D effluent was then loaded into RP #2, while an equilibration solution was flushing through RP #1 to wash away the matrix (including IEX eluent) from sample loading. At that moment, a gradient eluent was still running through RP #3. From t=20 min to t=25 min, the left stream selector was switched to Position 5 (see FIG. 5(d)). While the first-D effluent was still loaded into RP #2, gradient separation in RP #1 started. At that time, an equilibration solution was flushing through RP #3 to get it ready for sample loading. From t=25 min to t=35 min, the right stream selector 12a was switched to Position 1 (see FIG. 5E). The first-D effluent was then loaded into RP #3, an equilibration solution was flushing through RP #2 to wash away the matrix from sample loading, and a gradient eluent was running through RP #1 for separation. From t=35 min to t=40 min, the left stream selector 12b was switched to Position 1 (see FIG. 5F). The first-D effluent was still loaded into RP #3, gradient eluent was running through RP #2, and an equilibration solution was flushing through RP #1 to get it ready for sample loading. After 45 min, the operation cycled back to the configuration as shown in FIG. 5A.

As a result of the above operation, every column was loaded with the first-D effluent (or sample) for 15 min, washed with the equilibration solution for 5 min, eluted with the RP gradient for 15 min, and washed again with the equilibration solution for 10 min before being loaded with another sample.

Results and Discussion

RP-HPLC Separation

In a second-D RP-HPLC separation, we used a multi-step protocol (i.e., sample loading, matrix washing, analyte elution, and column equilibration). A column-equilibration step was important because the residual RP gradient in the column would interfere with the sample loading. The matrix washing step was also important because some matrix compounds such as lipids and carbohydrates interfered with RP-HPLC separation and absorption detection. This step is useful when MS is used as a detector when the first-D eluent contains an amount of salt that could interfere with MS measurements.

Column Preparation for 2D HPLC

A capillary (250-μm i.d.) was constructed for use as a monolithic column. An ion exchange (IEX) column was used for the first-D and multiple RP columns were used for the second-D. In one non-limiting method, an IEX column was prepared using a two-step procedure (see Paul, S. & Ranby, B. Methyl methacrylate (MMA)-glycidyl methacrylate (GMA) copolymers. A novel method to introduce sulfonic acid groups on the polymeric chains. *Macromolecules* 9, 337-340 (1976); and Sabarudin, A., Huang, J., Shu, S., Sakagawa, S. & Umemura, T. Preparation of methacrylate-based anion-exchange monolithic microbore column for chromatographic separation of DNA fragments and oligonucleotides. *Anal. Chim. Acta* 736, 108-114 (2012)). Briefly, a co-polymer monolith was first synthesized by in-situ polymerization of glycidyl methacrylate and Ethylene glycol dimethacrylate in a 250-μm i.d. vinylized capillary. Tertiary-amine groups were then introduced into the monolith to serve as weak anion-exchanger via a ring-opening reaction of the epoxy groups.

Figure 1B:
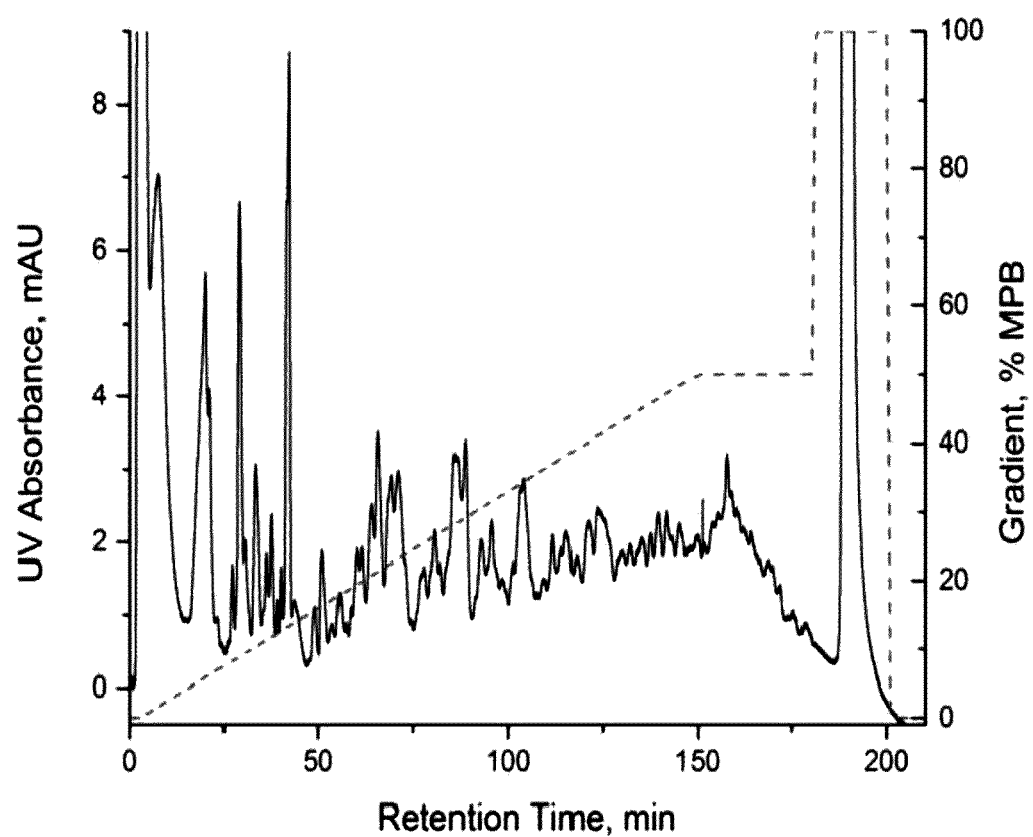
FIG. 1B. Performance of IEX chromatography: Separation of protein lysates from *E. coli* cells. The pressure on the column was ~1900 psi. Column construction and all other conditions were as in FIG. 1A.

FIGS. 1A and 1B show two chromatograms when this column was used to separate a standard protein mixture (FIG. 1A) and a protein lysate sample from *E. coli* cells (FIG. 1B). Baseline separation is achieved for the standard protein mixture (FIG. 1A) while more than 70 peaks were identifiable for the *E. coli* lysates (FIG. 1B); these are excellent results for separating proteins using monolith columns.

Figure 2A:
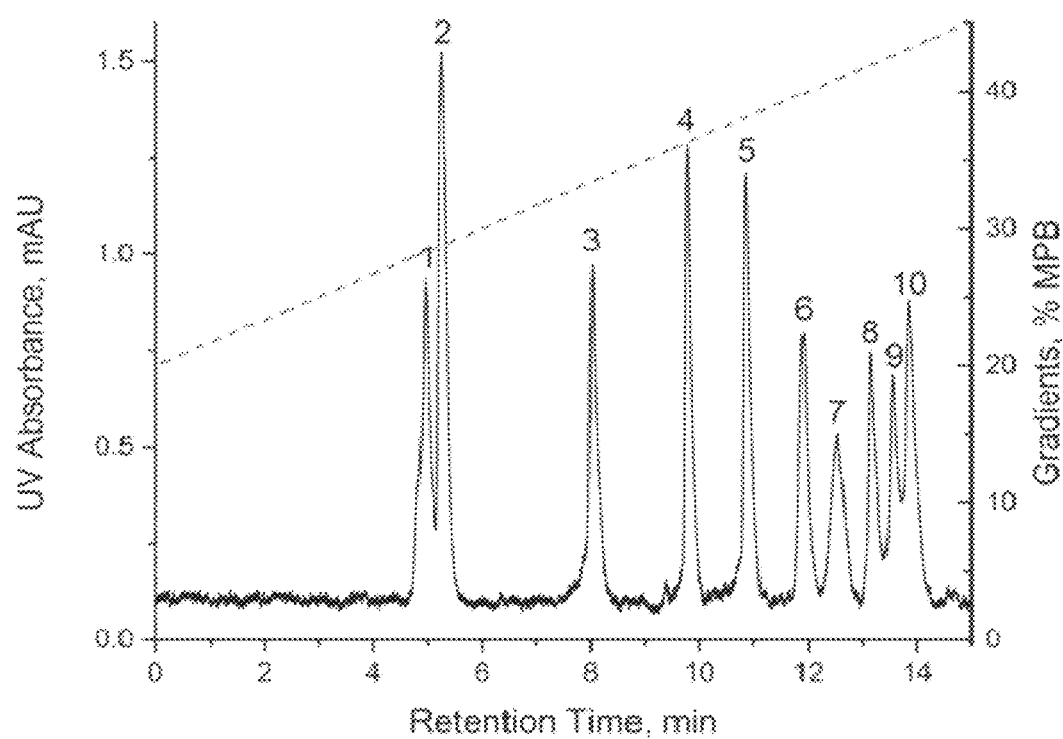
FIG. 2A. Performance of RP HPLC. Separation of protein standards. The monolithic column was of 20-cm length, 360-μm o.d. and 250-μm i.d. and it was made in laboratory. Mobile phase A, 5% (v/v) acetonitrile and 0.05% (v/v) tetrafluoric acid in DDI water; mobile phase B, 90% (v/v) acetonitrile and 0.05% (v/v) tetrafluoric acid in DDI water. Gradient, as indicated with the dashed line in the figure; detection, UV at 210 nm; injection volume, 50 nL; sample, a mixture of ribonuclease a (a), insulin (2), cytochrome c (3), lysozyme (4), α-lactalbumin (5), transferrin (6), conalbumin (7), myoglobin (8), β-lactoglobulin b (9) & a (10); each at 200 μg/mL; pressure on column, ~1100 psi.
Figure 2B:
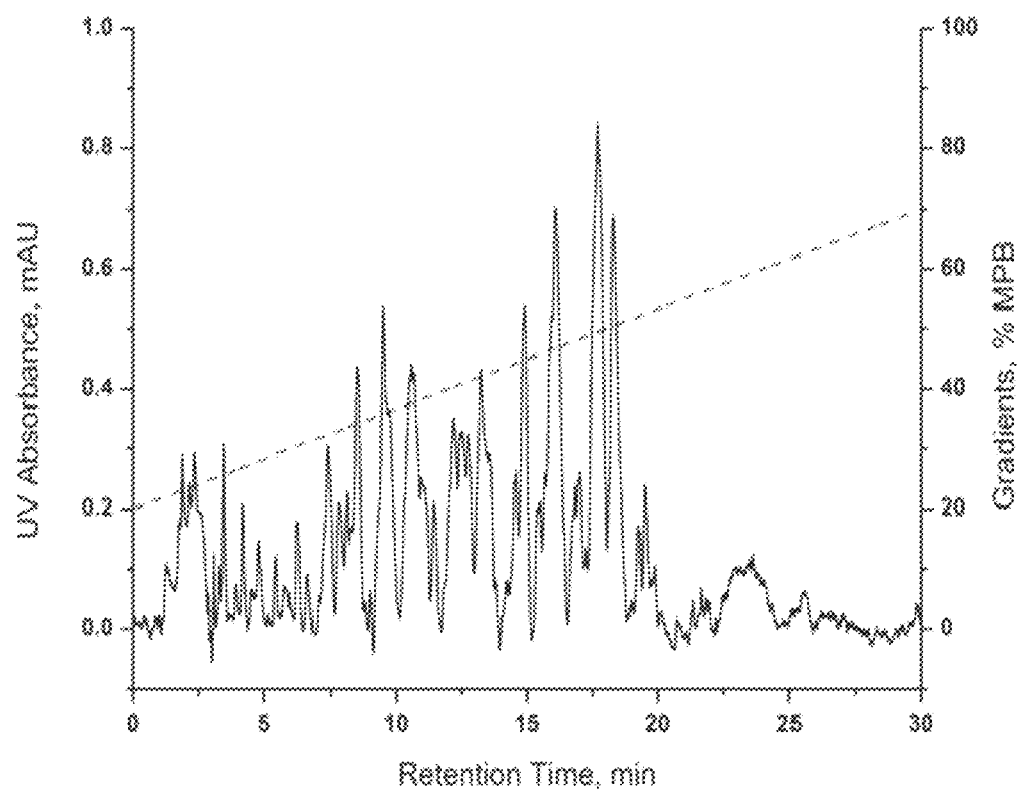
FIG. 2B. Performance of RP HPLC: Separation of protein lysates from *E. Coli* cells. The gradient was indicated with the dashed line in the figure. Detection, UV at 210 nm. Sample, 70-fold diluted protein lysates from *E. coli* cells. Pressure on column, ~1100 psi; Column construction and all other conditions were as in FIG. 2A.
Figure 6:
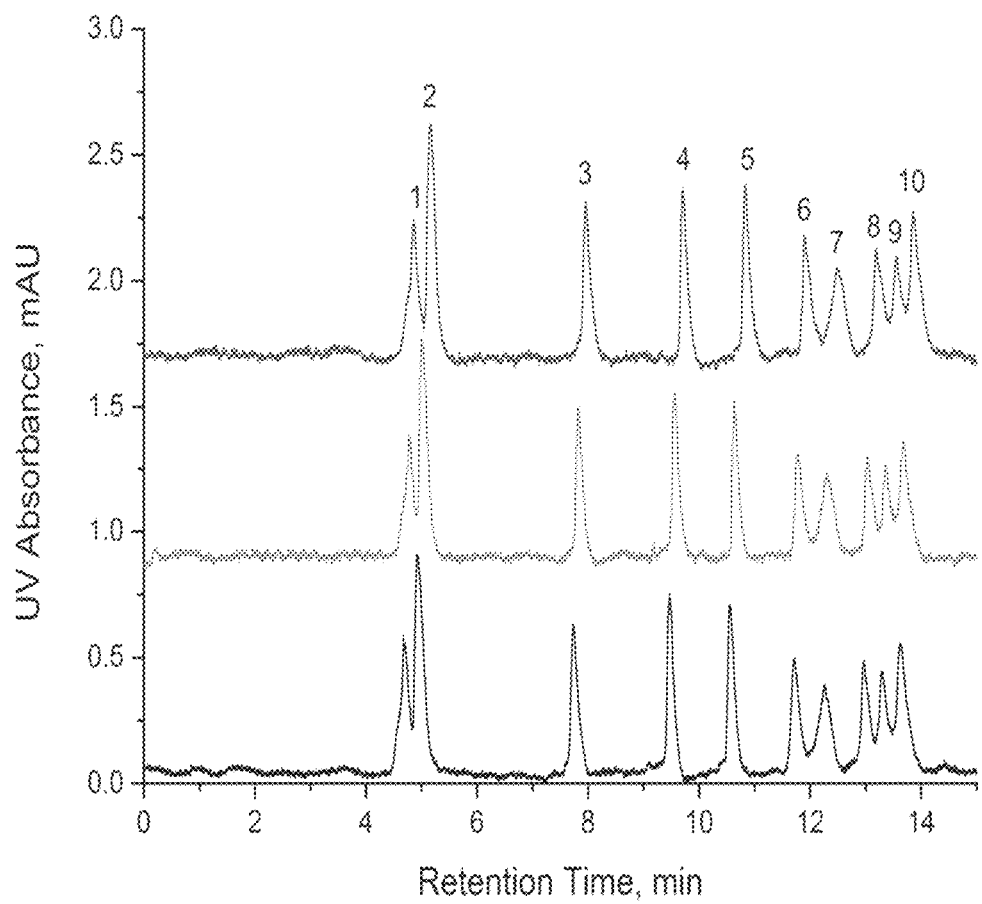
FIG. 6. Column-to-column reproducibility in RP HPLC. Three monolithic columns were simultaneously made in the laboratory. Each column was of 20-cm length, 360-μm o.d. and 250-μm i.d. Mobile phase A, 5% (v/v) acetonitrile and 0.05% (v/v) tetrafluoric acid in DDI water; mobile phase B, 90% (v/v) acetonitrile and 0.05% (v/v) tetrafluoric acid in DDI water. Gradient, as indicated with the dashed line in the figure; detection, UV at 280 nm; injection volume, 50 nL; sample, a mixture of ribonuclease a (a), insulin (2), cytochrome c (3), lysozyme (4), α-lactalbumin (5), transferrin (6), conalbumin (7), myoglobin (8), β-lactoglobulin b (9) & a (10); each at 200 μg/mL; pressure on column, ~1100 psi.
Figure 7:
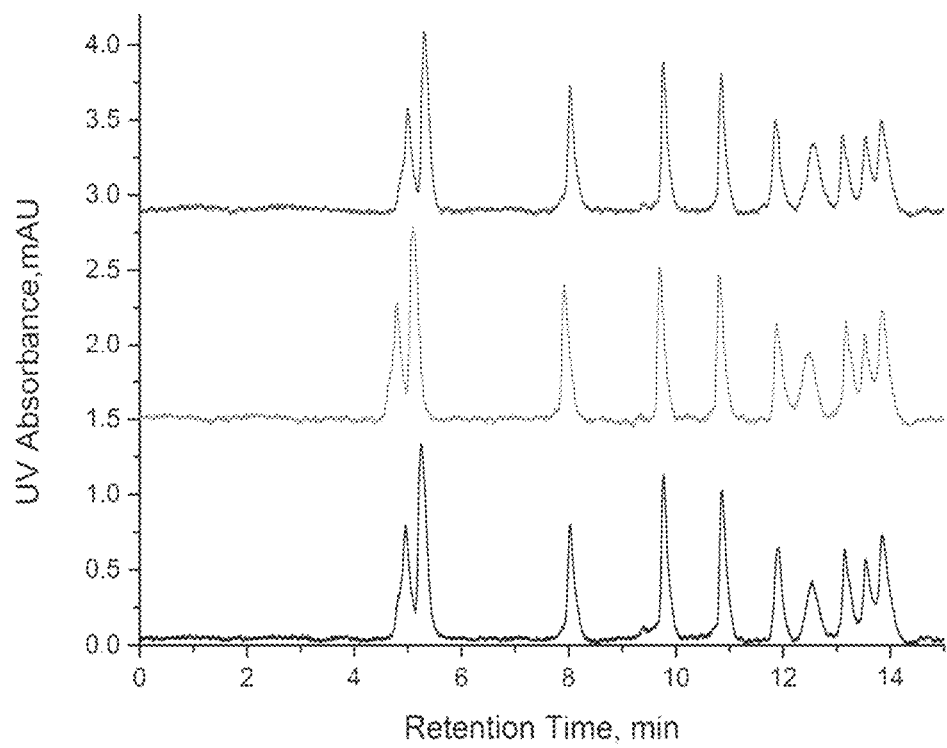
FIG. 7. Batch-to-batch reproducibility in RP HPLC. Three batches of monolithic monolithic columns were made in different days. All experimental conditions were as in FIG. 6.

RP columns comprising, in a non-limiting embodiment, polystyrene/polydivinylbenzene-based monolithic columns were prepared following a procedure published previously in the literature (see Premstaller, A., et al. High-performance liquid chromatography-electrospray ionization mass spectrometry using monolithic capillary columns for proteomic studies. *Anal. Chem.* 73, 2390-2396 (2001)). Both standard proteins (FIG. 2A) and *E. coli* cell lysates (FIG. 2B) were separated using this column; high quality results were obtained as well. FIG. 6 presents the performance comparison between columns of the same batch and FIG. 7 shows the comparison between columns from three different batches using the same sample. Similar results were obtained.

Second-D Separation Speed Consideration

A conventional 2D HPLC system usually consists of one first-D column and one second-D column. In a comprehensive 2D separation, the first-D effluent is continuously segmented and injected into the second-D column for analysis. If the separation time of the first-D is t and its effluent is segmented into n fractions, the separation time for the second-D should be t/n or less. This constraint imposes a great challenge for utilizing optimum conditions for both separation dimensions.

Figure 8:
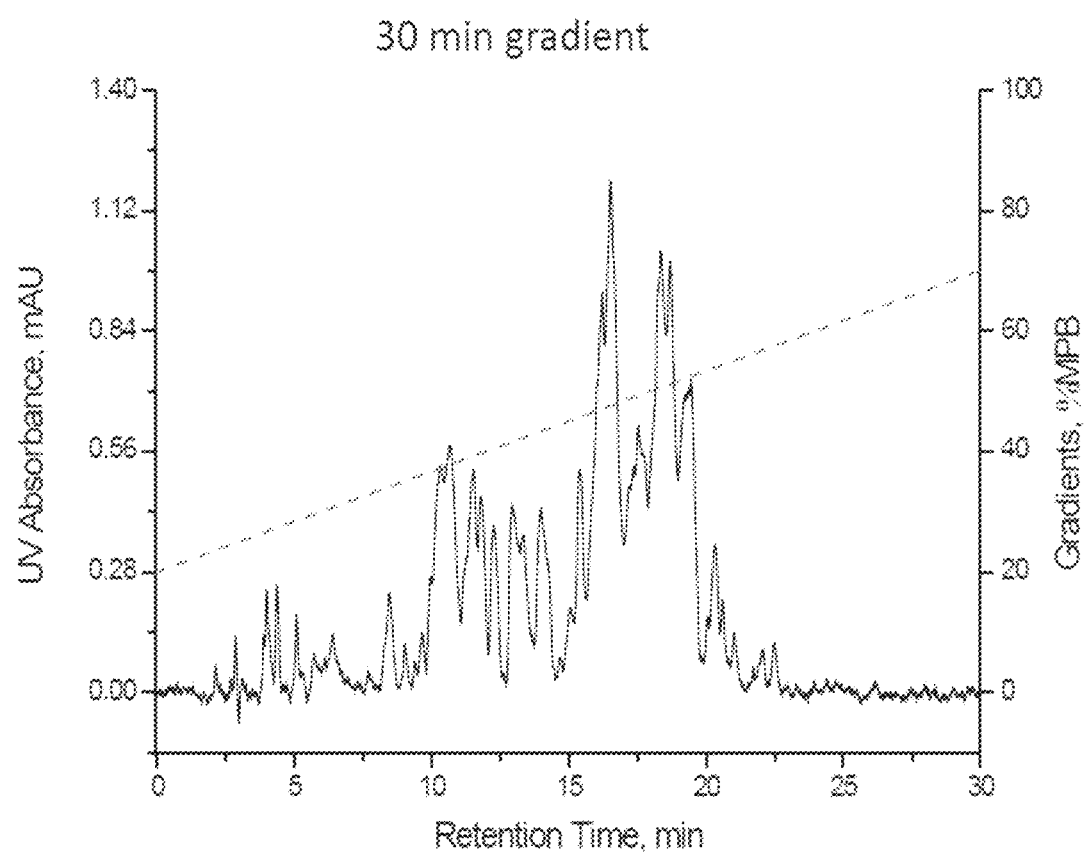
FIG. 8. Separation of protein lysates from *E. coli* cells with RP HPLC. A gradient of 30 minutes was used to demonstrate the effect of the gradient ramp rate on the separation performance. The gradient was indicated with the dashed line in its corresponding figure. Sample, 70-fold diluted protein lysates from *E. coli* cells. All other conditions were as in FIG. 6.
Figure 9:
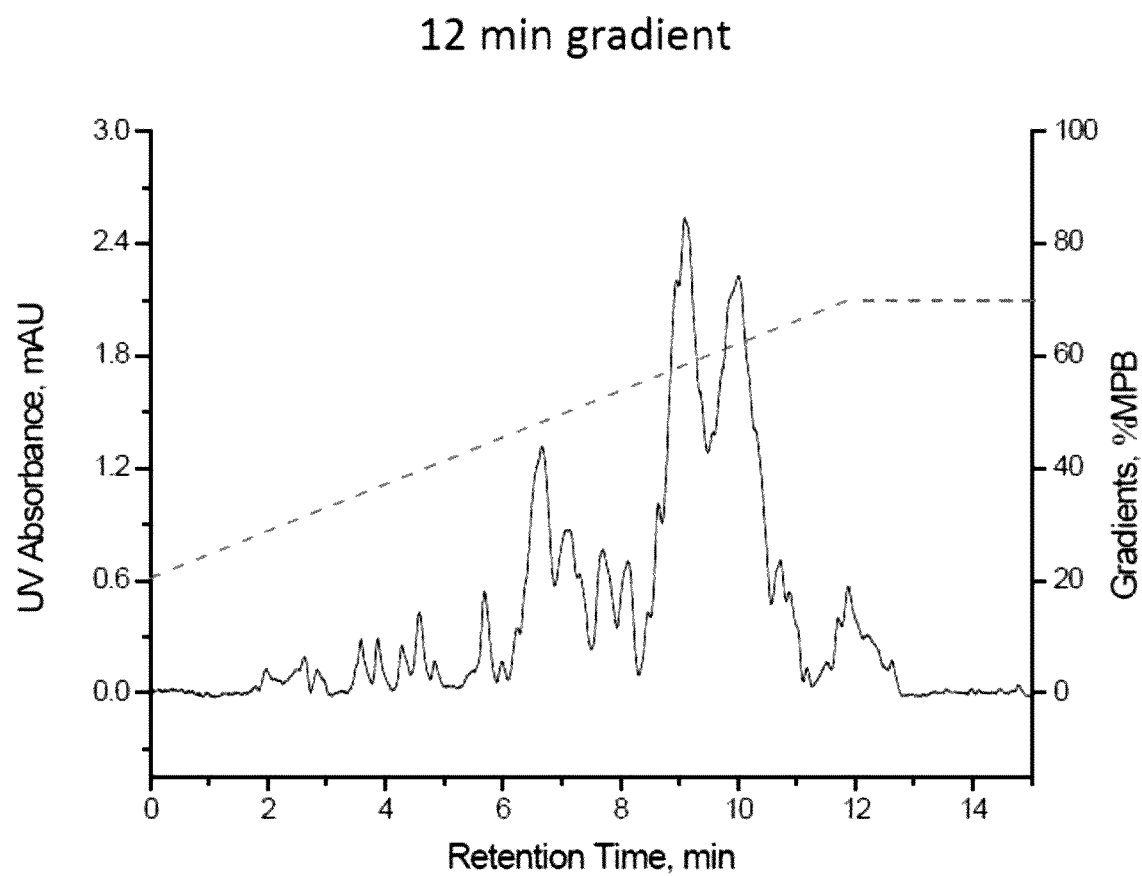
FIG. 9. Separation of protein lysates from *E. coli* cells with RP HPLC. A gradient of 12 minutes was used to demonstrate the effect of the gradient ramp rate on the separation performance. The gradient was indicated with the dashed line in its corresponding figure. Sample, 70-fold diluted protein lysates from *E. coli* cells. All other conditions were as in FIG. 6.
Figure 10:
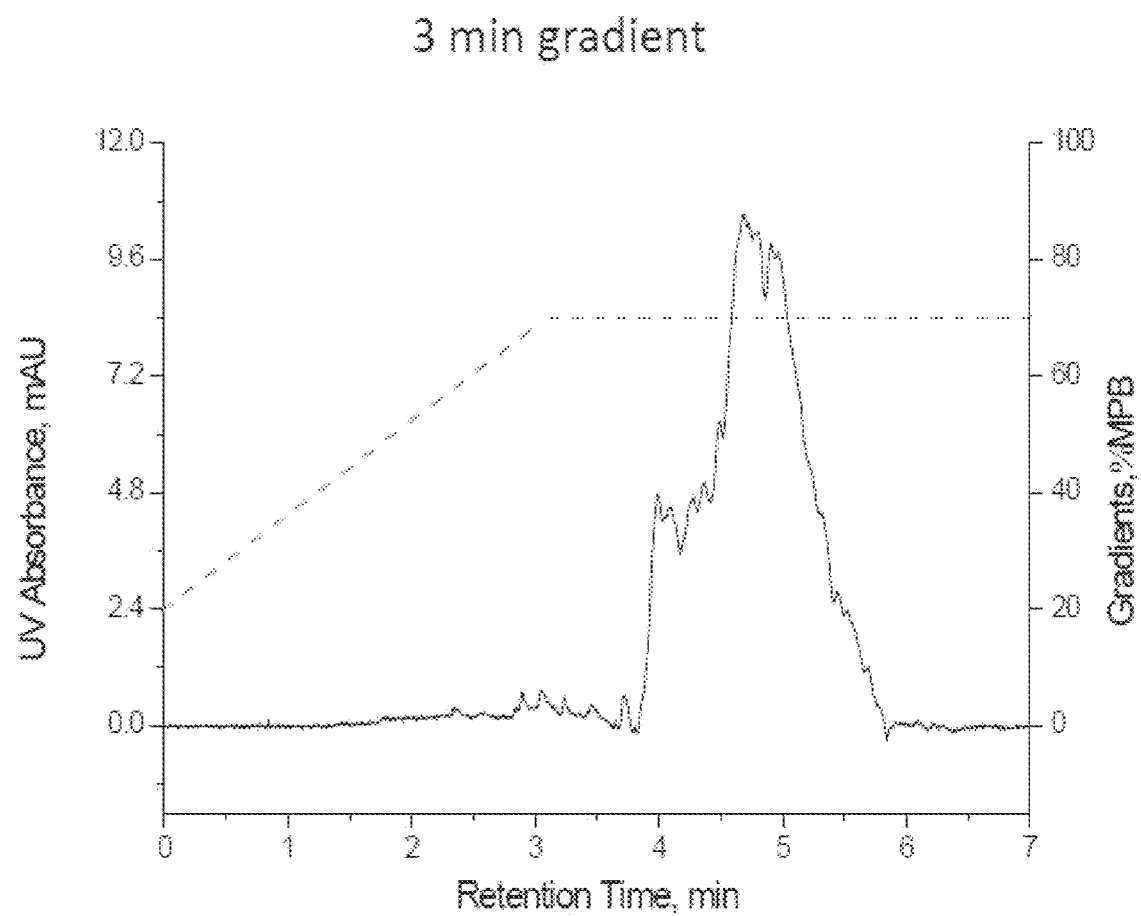
FIG. 10. Separation of protein lysates from *E. coli* cells with RP HPLC. A gradient of 3 minutes was used to demonstrate the effect of the gradient ramp rate on the separation performance. The gradient was indicated with the dashed line in its corresponding figure. Sample, 70-fold diluted protein lysates from *E. coli* cells. All other conditions were as in FIG. 6.
Figure 11:
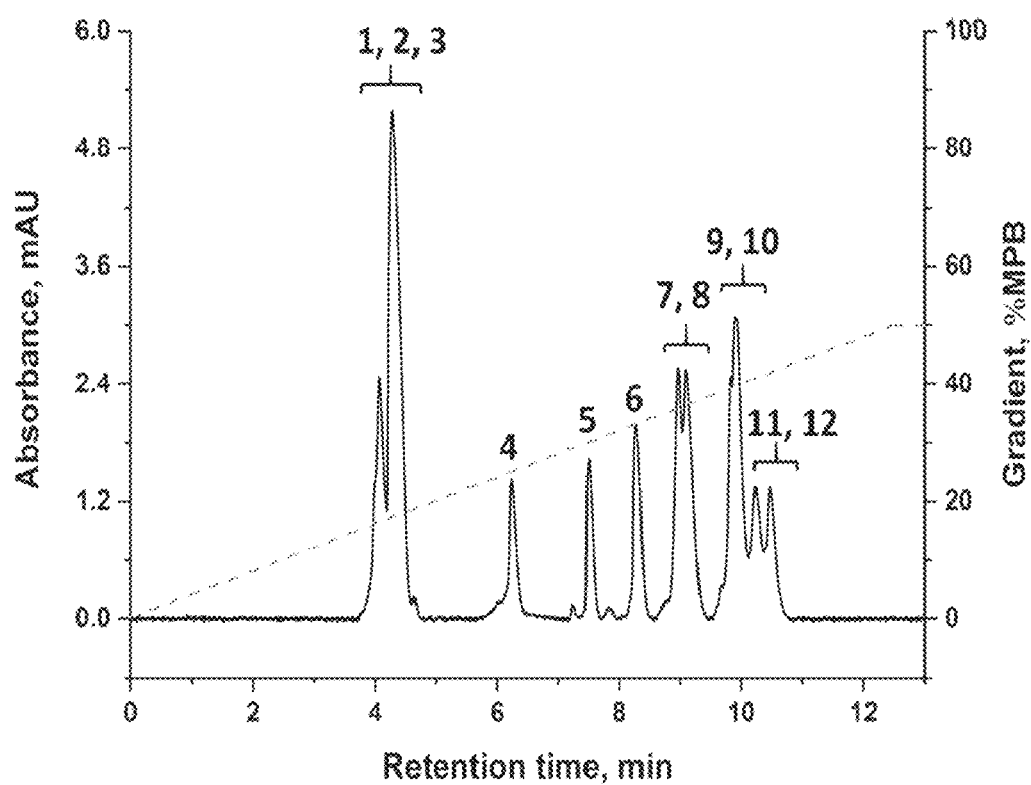
FIG. 11. Testing the 2D HPLC platform with protein standards: Separation of protein standards with RP HPLC. Gradient, as indicated with the dashed line in the figure; sample, a mixture of ribonuclease a (1), ovalbumin (2), insulin (3), cytochrome c (4), lysozyme (5), α-lactalbumin (6), transferrin (7), trypsin inhibitor (8), myoglobin (9), conalbumin (10), β-lactoglobulin b (11) and a (12); each at 4 μg/mL; all other conditions were as in FIG. 6.

Here we present an example showing the adverse effect of this constraint. As can be seen in FIGS. 1A-2B, both IEX and RP columns exhibited reasonable resolving power for intact proteins under optimized conditions. In order to retain the resolution of the first-D, we would like to segment its effluent into 100 aliquots for the second-D separations. We would also like to run the second-D separations in a continuous fashion, i.e., no fractionated solution parking. If one IEX column and one RP column were used for the first-D and second-D, we would have to finish each second-D separation in less than 2 min based on the chromatogram in FIG. 11B. FIGS. 8-10 presents three chromatograms of different gradient ramp rates (30, 12, and 3 minutes, respectively). Resolutions deteriorated seriously as the ramp rate increased. Apparently, we could not utilize any parameters close to optimized conditions in such a 2D HPLC system based on single columns in each dimension.

Use of Multiple Columns to Address Second-D Speed Demand

We considered a possible solution to mitigate the speed constraint by incorporating parallel columns in the second-D so that the first-D effluent could be analyzed simultaneously by multiple columns. For the aforementioned example, we determined that if we could arrange 20 columns in the second-D to run separations simultaneously, the time required for each separation would increase to 40 min, which would allow us to utilize the optimized separations conditions in both dimensions.

Figure 3:
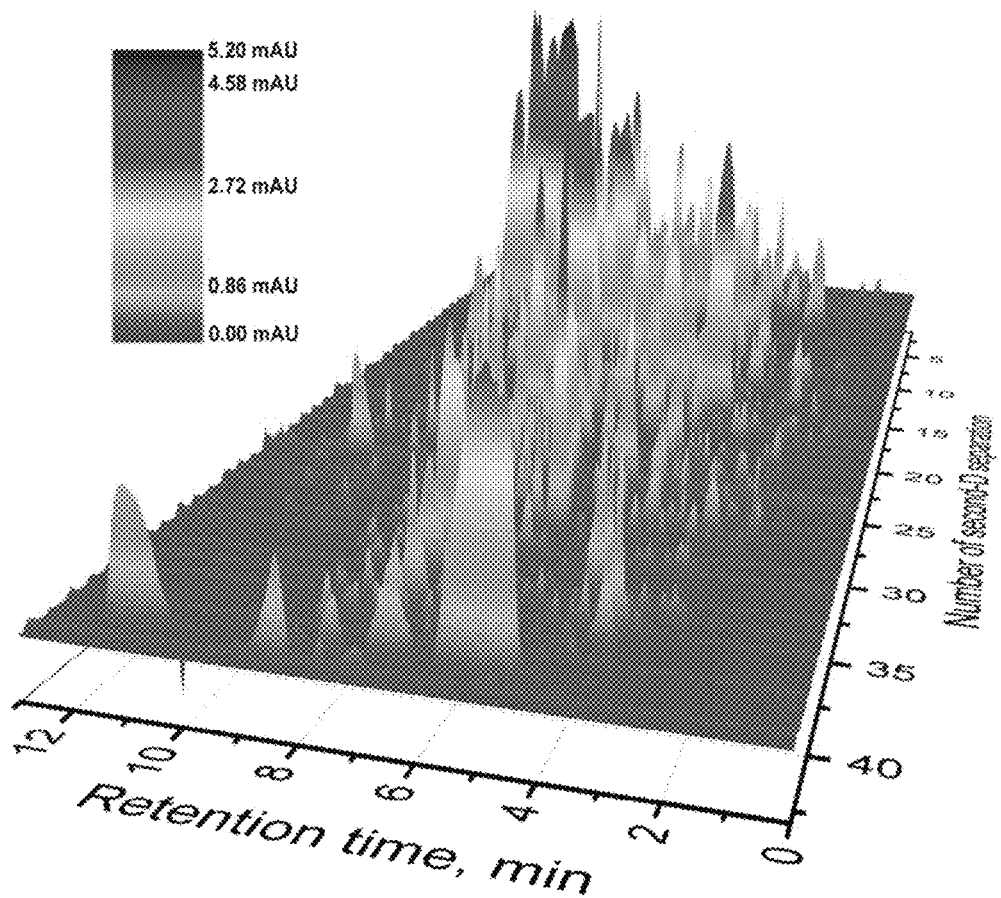
FIG. 3. Separation of protein lysates from *E. coli* cells using the 2D HPLC platform. Sample—*E. coli* cells lysates; IEX and RP column length—20 cm; Separation pressure for the first-D: 3500 psi; Separation pressure for the second-D: 1100 psi; The first-D gradient: [NaCl] increased linearly from 0-0.5 M in 600 min, increased from 0.5-1 M in 0.1 min, and kept at 1 M for 30 min; The first-D injection volume: 20 μL; The gradients for the second-D separations are presented in Table 1.

To demonstrate the feasibility of this approach, we incorporated three columns in the second-D. However, including only three second-D columns would not allow us to run both separation dimensions at their optimized conditions. As a compromise for this three-second-D column setup, we extended the first-D separation to 10.5 h and shortened the second-D separation to 15 min. With this set of conditions, we could fractionate the first-D effluent into 42 fractions. FIG. 3 presents the 2D separation results for *E. coli* cell lysates under these conditions. Greater than 500 peaks were obtained, even though only three columns were incorporated in the second-D. Different gradients were used for the second-D separations in this experiment, and the detailed gradient conditions are listed in Table 1.

TABLE 1

| Gradients used in the second dimension | |
| --- | --- |
| Fractions | Gradients, % MPB |
| 1-7 | 25-55 |
| 8-14 | 28-58 |
| 15-21 | 31-61 |
| 22-28 | 34-64 |
| 29-35 | 37-67 |
| 36-42 | 40-70 |

MPA, 5% (v/v) acetonitrile and 0.05% (v/v) tetrafluoric acid in DDI water; MPB, 90% (v/v) acetonitrile and 0.05% (v/v) tetrafluoric acid in DDI water. 14-min gradients were used for protein separations and the pump was conditioned with MPA for one minute between two gradients.

Sample Complexity Reduction after 2D Separation

Figure 4:
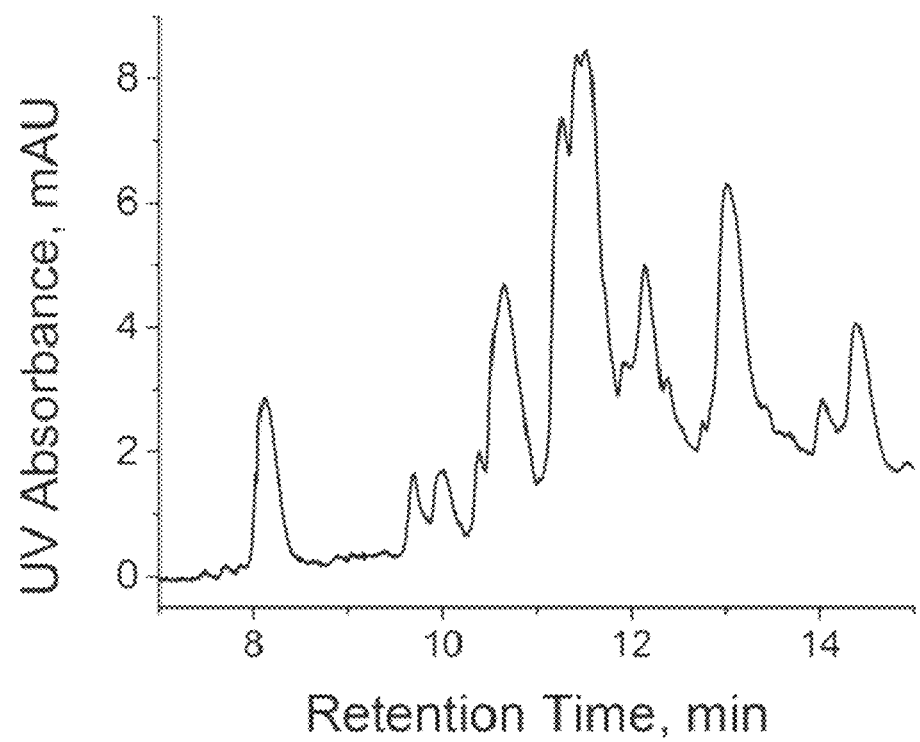
FIG. 4. Typical sample complexity after 2D HPLC separation. Bottom: a second-D chromatogram (the seventh RP separation from FIG. 3); Top: SDS-PAGE results of six effluent fractions (the fractions were collected from 8-15 min retention time, and each fraction was collected for 70 s). Electrophoretic separation was performed using Mini-PROTEIN® Electrophoresis System (Bio-Rad, Hercules, Calif.) at 200 volts for 40 min. The gel contained 12% acrylamide. The image was created using silver stain. The positions of the sample in the SDS-PAGE gel image matched vertically with the retention time of the chromatogram.

To determine the sample complexity after 2D separation, the effluents from the second-D were collected and analyzed by SDS-PAGE. As shown in FIG. 4, several bands were observed in SDS-PAGE, indicating that multiple proteins still existed in each of these samples. Significantly, only several bands were observed in any lane; compared to hundreds or thousands of proteins in the original sample, thus the sample complexities were greatly reduced. These samples can be conveniently analyzed by MS. The number of proteins in each sample will be reduced proportionally as the number of the columns used in the second-D is increased.

Figure 12:
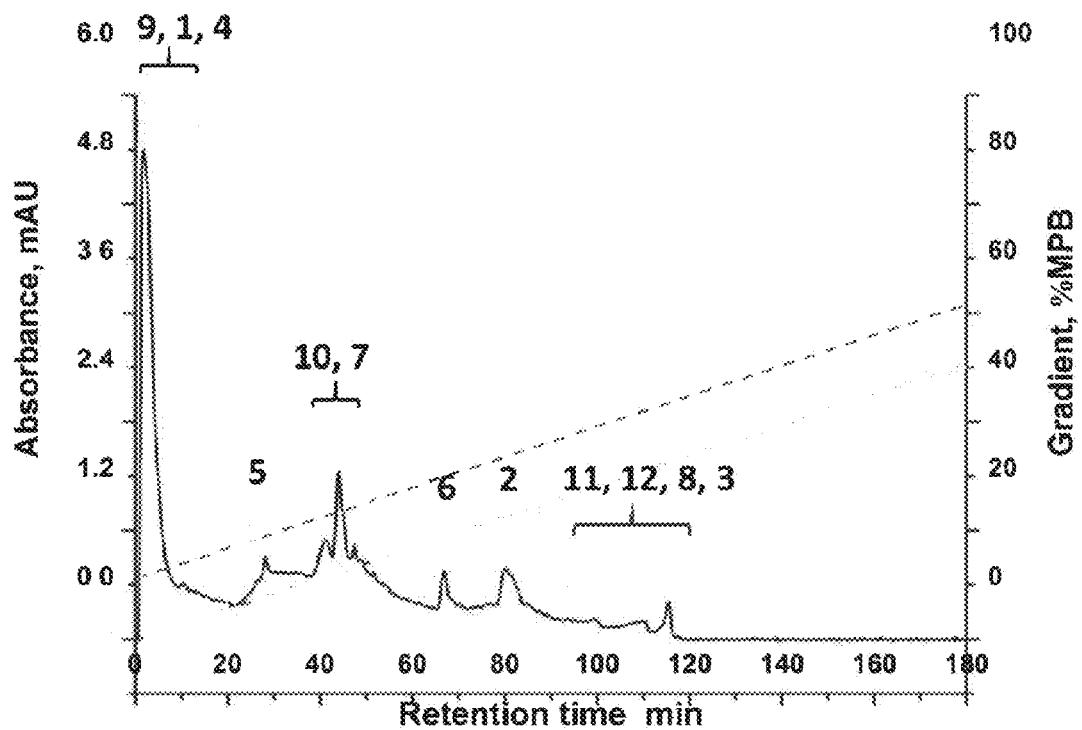
FIG. 12. Testing the 2D HPLC platform with protein standards: Separation of protein standards with IEX chromatography. The column was a monolithic one made in laboratory. It was of 20-cm length, 360-μm o.d. and 250-μm i.d. Mobile phase A, 10 mM Tris/HCl at pH ~7.6 in DDI water; mobile phase B, 1 M NaCl dissolved in mobile phase A. Gradient, as indicated with the dashed line in the figure; detection, UV at 280 nm; injection volume, 20 μL; sample, a mixture of ribonuclease a (1), ovalbumin (2), insulin (3), cytochrome c (4), lysozyme (5), α-lactalbumin (6), transferrin (7), Trypsin inhibitor (8), myoglobin (9), conalbumin (10), β-lactoglobulin b (11) & a (12); each at 50 μg/mL; pressure on column, ~1900 psi.
Figure 13:
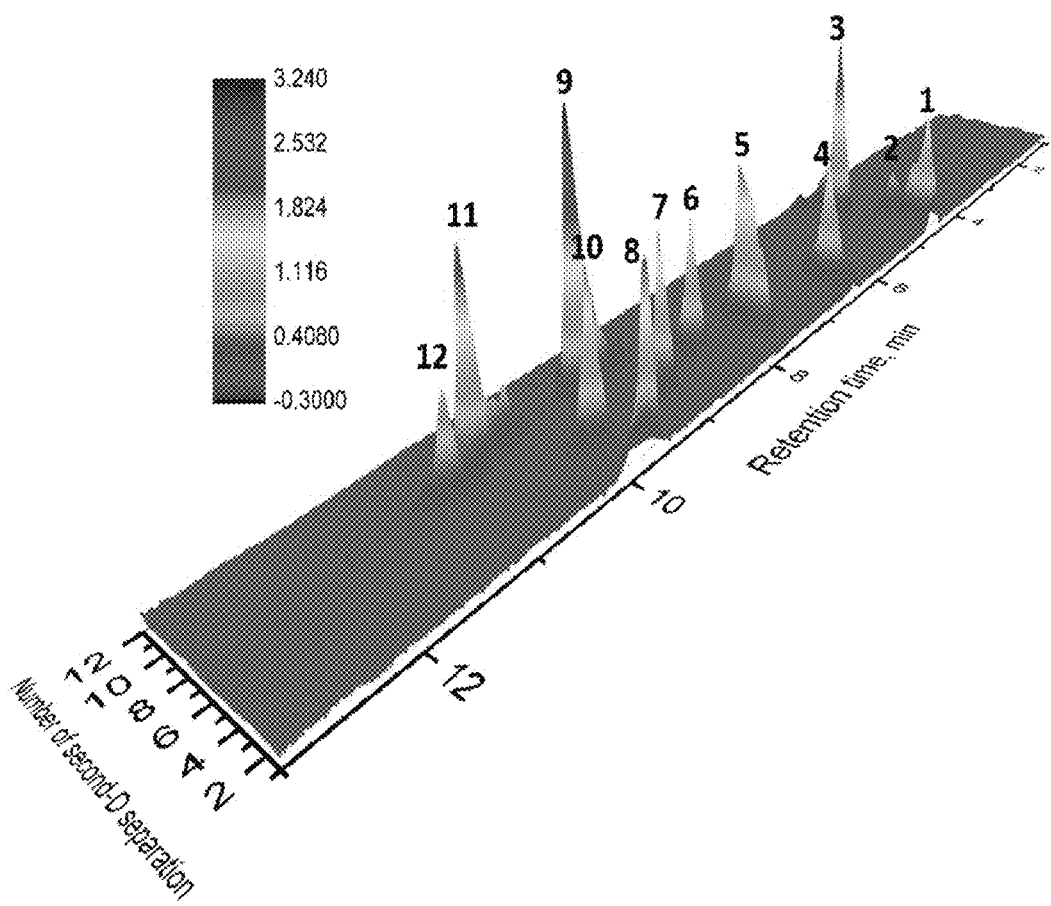
FIG. 13. Testing the 2D HPLC platform with protein standards: Separation of standard proteins with the new developed 2D HPLC platform. The second-dimension chromatograms was stacked side by side in the order of fraction number, which was assembled using Origin. Injection volume, 20 μL; sample, a mixture of ribonuclease a (1), ovalbumin (2), insulin (3), cytochrome c (4), lysozyme (5), α-lactalbumin (6), transferrin (7), Trypsin inhibitor (8), myoglobin (9), conalbumin (10), β-lactoglobulin b (11) & a (12); each at 4 μg/mL. The length of each RP column, and IEX column was 20 cm. The pressure was ~3500 psi on IEX Pump and ~1100 psi on RP Pump. The gradients for the first and second dimensions were as in FIGS. 11-12, respectively.

As described above, in at least one embodiment, we coupled a first separation column (e.g., IEX chromatography) as a first-D with multiple-column RP HPLC chromatography as a second-D for comprehensive 2D separation of intact proteins. With n columns incorporated in the second-D, the time requirement of the second-D is reduced by a factor of up to n. To demonstrate the feasibility of this approach, we incorporated three second-D columns, and reduced the time requirement (increased the speed) of the second-D separation step by a factor of 3. This system was tested for separating both protein standards and *E. coli* lysates; baseline resolutions were obtained for separating 11 standard proteins (see FIGS. 11-13) while more than 500 protein peaks were detected for the *E. coli* lysate sample. We collected the second-D effluents from separating *E. coli* lysates and analyzed these samples by SDS-PAGE. Only several proteins were found in each of these samples, and these samples can be easily analyzed by MS or other techniques. The number of proteins in each sample would further decrease as the number of the second-D columns increases. This approach provides an excellent technique for reducing the complexities of real-world proteomic samples, particularly when integrated with a mass spectrometer.

Example 2

Alternate Embodiment of an Online 2D HPLC Platform

To further improve throughput of protein analysis, another online 2D HPLC apparatus 100 was tested. As shown in the FIGS. 14A and 14B, IEX was used as the first-D, and RP chromatography was used as second-D. The second-D included 12 RP columns and two custom-designed valves (V1 and V2), so that six RP separation steps and six-fraction loading steps could be performed simultaneously, resulting in improved resolutions and increased throughput.

The apparatus 100 has two gradient pumps 102a and 102b (IEX Pump—Dionex GP50 Gradient Pump, RP Pump—Agilent 1200 Series Binary Pump), one 20-μL injector 104, one four-port switching valve (Vs) 106 and two custom-designed stream selectors (V1) 108a and (V2) 108b, Valco Instruments, Houston, Tex.), and Laboratory-made multi-channel UV/Vis detectors 110. RP #1, #2, #3, #4, #5 and #6 columns are connected to V1, and RP #1', #2', #3', #4', #5', and #6' are connected to V2. Restriction capillaries (RC) are used to control the pressure on respective columns. All the (IEX and RP) monolithic columns are prepared with capillaries (250-μm i.d.).

Figure 14A:
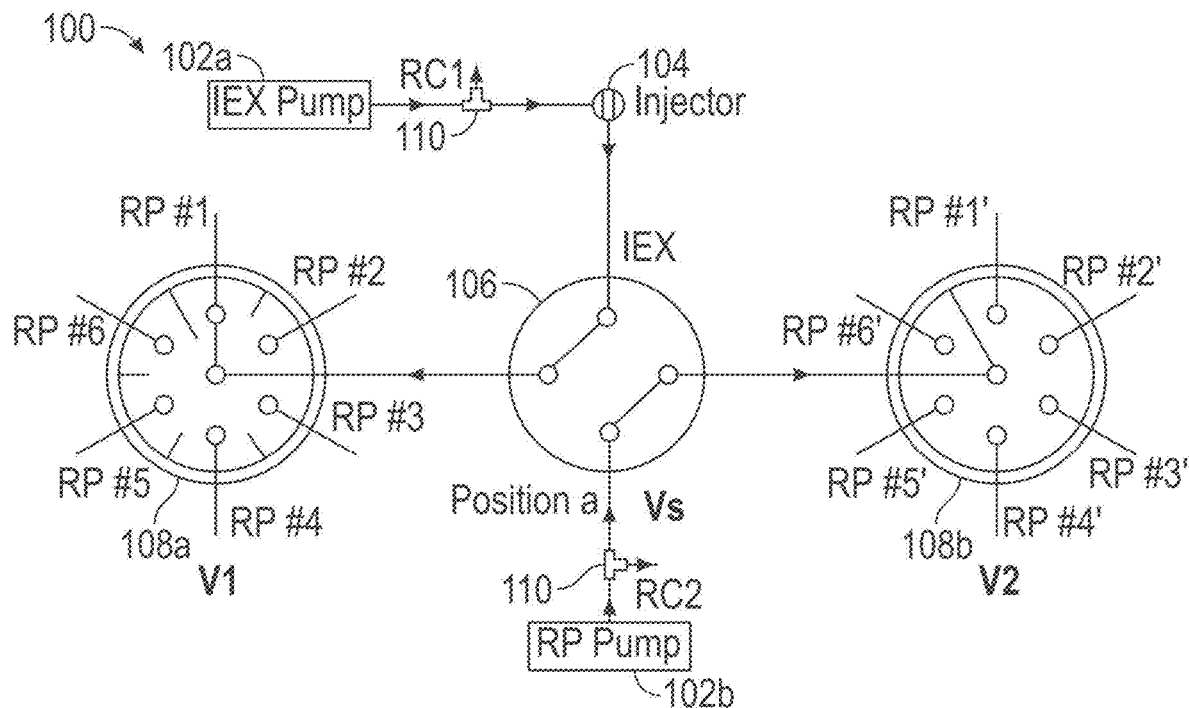
FIG. 14A is a schematic diagram of another embodiment of a 2D HPLC apparatus in a first mode of operation.
Figure 14B:
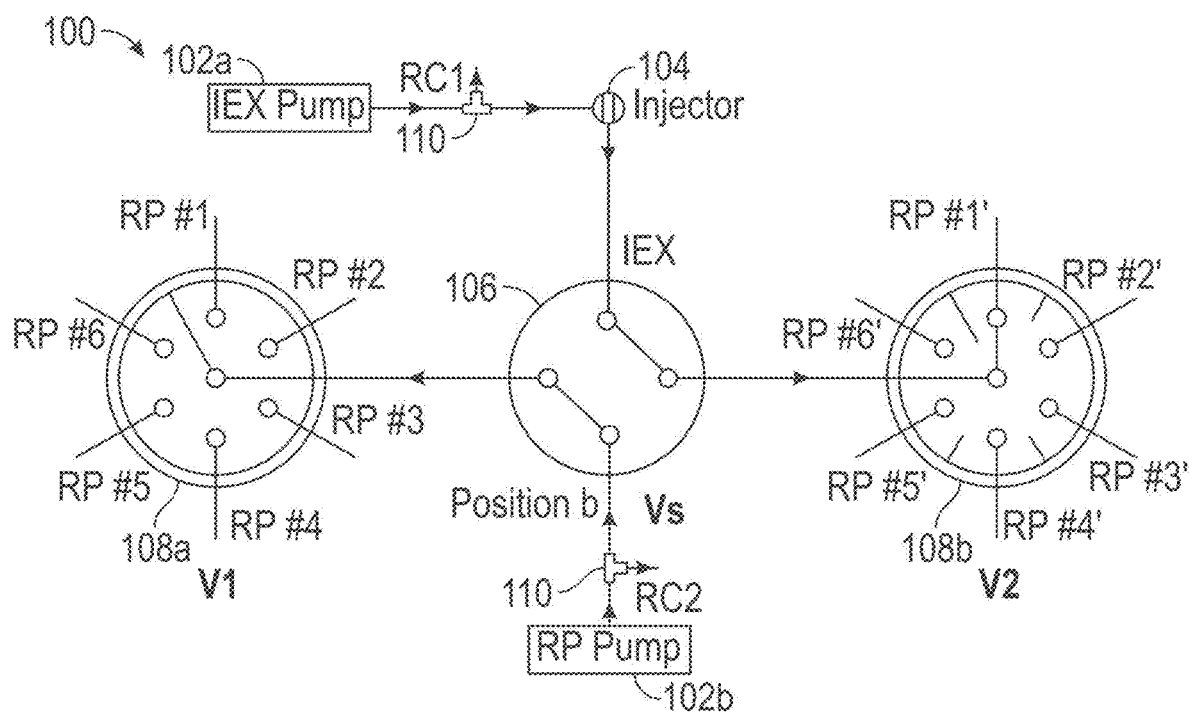
FIG. 14B is a schematic diagram of the 2D HPLC apparatus of FIG. 14B in a second mode of operation.

The configurations are shown in the FIGS. 14A and 14B. Once the gradient is started in the first-D (t=0 min), the effluent from IEX column can be loaded onto the six RP columns attached to V1 consecutively (e.g., 4 min each) by switching V1 (see FIG. 14A). After 24 min, Vs is switched to Position b (see FIG. 14B), and the IEX effluent is loaded onto the six RP columns attached to V2 consecutively (e.g., 4 min each) by switching V2; all the six columns are loaded with samples at t=48 min. Meanwhile (at t=24 min), V1 is switched to a common-port position; all six RP columns on V1 are eluted from t=24 min to t=48 min. At 48 min, the three valves (V1, Vs and V2) are switched back to the positions as shown in A; while samples are loaded to columns attached to V1 all the six columns attached to V2 are eluted.

What is claimed is:

1. A two-dimensional liquid chromatography (2D-LC) apparatus, comprising:
    a first dimension (first-D) comprising at least one first chromatography column;
    a second dimension (second-D) comprising a plurality of second chromatography columns;
    a pump; and
    a stream selector valve interposed between the first chromatography column, the plurality of second chromatography columns, and the pump, the stream selector valve having a plurality of loading positions and a separation position, in the loading positions the first chromatography column is in fluid communication with the second chromatography columns in a way that a plurality of effluent fractions outputted from the first chromatography column are loaded into the second chromatography columns consecutively, in the separation position the pump is in fluid communication with each of the second chromatography columns to effect simultaneous chromatographic separation by the second chromatography columns of the plurality of effluent fractions outputted from the first chromatography column.

2. The 2D-LC apparatus of claim 1, wherein the first dimension has a mode of chromatography selected from the group consisting of size exclusion chromatography, ion exchange chromatography, normal phase chromatography, reversed phase chromatography, hydrophilic interaction chromatography, hydrophobic interaction chromatography, affinity chromatography, argentation chromatography, and critical condition chromatography.

3. The 2D-LC apparatus of claim 1, wherein the second dimension has a mode of chromatography selected from the group consisting of size exclusion chromatography, ion exchange chromatography, normal phase chromatography, reversed phase chromatography, hydrophilic interaction chromatography, hydrophobic interaction chromatography, affinity chromatography, argentation chromatography, and critical condition chromatography.

4. A method of liquid chromatography analysis, comprising injecting a sample into the apparatus of claim 1, and analyzing the effluent fractions therefrom.

5. The 2D-LC apparatus of claim 1, wherein the plurality of second chromatography columns is a first plurality of second chromatography columns, wherein the stream selector valve is a first stream selector valve, wherein the plurality of effluent fractions outputted from the first chromatography column is a first plurality of effluent fractions outputted from the first chromatography column, and wherein the 2D-LC apparatus further comprises:
    a second plurality of second chromatography columns;
    a second stream selector valve interposed between the first chromatography column, the second plurality of second chromatography columns, and the pump, the second stream selector valve having a plurality of loading positions and a separation position, in the loading positions the first chromatography column is in fluid communication with the second plurality of second chromatography columns in a way that a second plurality of effluent fractions outputted from the first chromatography column are loaded into the second plurality of second chromatography columns consecutively, in the separation position the pump is in fluid communication with each of the second plurality of second chromatography columns to effect simultaneous chromatographic separation by the second plurality of second chromatography columns of the second plurality of effluent fractions outputted from the first chromatography column; and
    a switching valve interposed between the first chromatography column, the first stream selector valve, the second stream selector valve, and the pump, the switching valve having a first position wherein the first chromatography column is in fluid communication with the first plurality of second chromatography columns when the first selector valve is in the loading positions and the pump is in fluid communication with each of the second plurality of second chromatography columns when the second selector valve is in the separation position and a second position wherein the first chromatography column is in fluid communication with the second plurality of second chromatography columns when the second selector valve is in the loading positions and the pump is in fluid communication with the first plurality of second chromatographic columns when the first selector valve is in the separation position.

6. A method of liquid chromatography analysis, comprising injecting a sample into the apparatus of claim 5, and analyzing the effluent fractions therefrom.

* * * * *

UNITED STATES PATENT AND TRADEMARK OFFICE
CERTIFICATE OF CORRECTION

PATENT NO. : 10,732,154 B2  
APPLICATION NO. : 15/913043  
DATED : August 4, 2020  
INVENTOR(S) : Shaorong Liu and Zaifang Zhu Page 1 of 1

It is certified that error appears in the above-identified patent and that said Letters Patent is hereby corrected as shown below:

In the Specification  
Column 11, Line 39: Delete "FIG. 11B." and replace with -- FIG. 1B. --

Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*